Figure 1:
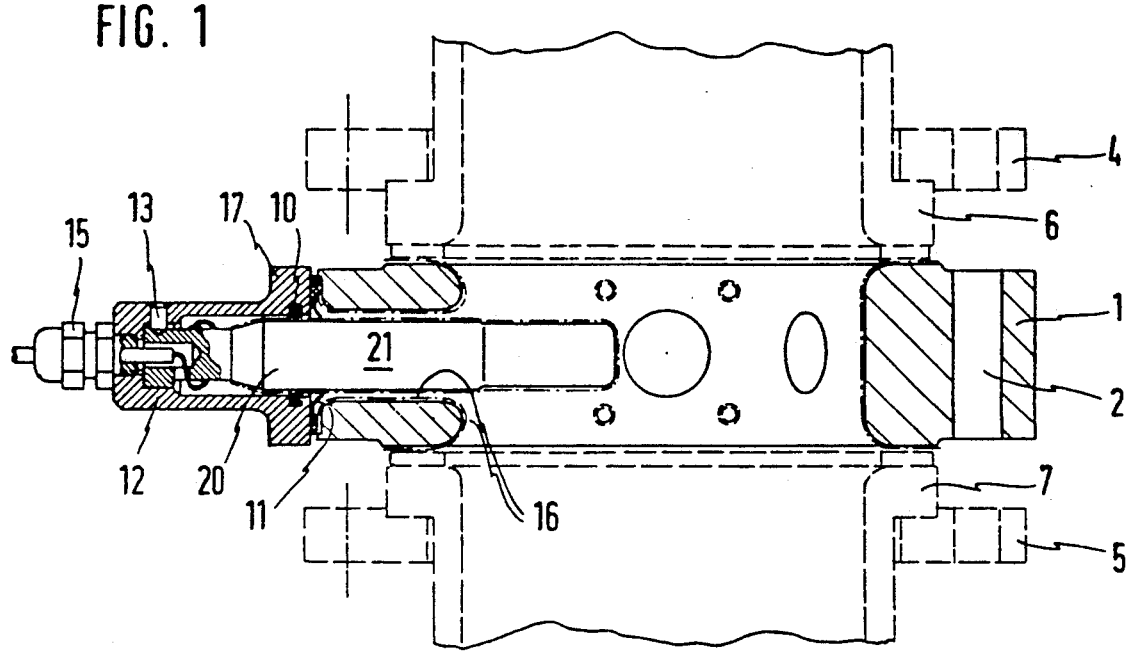

United States Patent [19]

Kohler et al.

[11] Patent Number: 5,082,367
[45] Date of Patent: Jan. 21, 1992

[54] ARRANGEMENT OF PROBES

[75] Inventors: Werner Kohler, Bruhl; Dieter Reinhardt, Walldorf; Hermann Gramlich, HaBloch; Reinhart Schertz, Oftersheim; Karl Weissmann, Oftersheim; Rainer Trampert, Oftersheim, all of Fed. Rep. of Germany

[73] Assignee: Pfaudler-Werke AG, Schwetzingen, Fed. Rep. of Germany

[21] Appl. No.: 358,691

[22] Filed: May 26, 1989

[30] Foreign Application Priority Data

Jun. 3, 1988 [DE] Fed. Rep. of Germany ....... 3819026

[51] Int. Cl.$^5$ .................... G01N 21/00; G01N 27/02
[52] U.S. Cl. ..................................... 356/73; 324/446
[58] Field of Search ................... 356/72–73.1; 350/96.1, 96.25, 96.26, 244–246; 128/4–8; 210/614, 638; 324/446, 72.5, 158 P; 357/440, 443

[56] References Cited

U.S. PATENT DOCUMENTS

| 3,810,695 | 5/1974 | Shea ........................... 356/73 |
| 4,146,799 | 3/1979 | Pitt et al. ..................... 250/575 |
| 4,201,471 | 5/1980 | Pitt et al. ..................... 356/73 |
| 4,753,530 | 6/1988 | Knight et al. ................. 356/73 |
| 4,788,506 | 11/1988 | Weissmann .................. 324/72.5 |
| 4,797,212 | 1/1989 | Von Nordenskjold ........ 210/614 |

FOREIGN PATENT DOCUMENTS 2133419 7/1971 Fed. Rep. of Germany.
2721939 1/1981 Fed. Rep. of Germany.

*Primary Examiner*—Richard A. Rosenberger
*Assistant Examiner*—Hoa Pham
*Attorney, Agent, or Firm*—Michael L. Dunn; Robert P. Simpson

[57] ABSTRACT

An arrangement of probes is described, which comprises a carrier formed as an intermediate flange, in which a plurality of radially extending mounting openings are provided. The inner surfaces of the carrier are provided with an electrically insulating corrosion resistant layer, which is preferably an enamel layer. The carrier is having a polygonal outline and plane mounting surfaces surrounding the mounting openings. Measuring probes provided with a mounting flange can be exchangeably and sealingly attached to the mounting surfaces. By arranging different probes a large number of different measurement functions and supervision functions can be achieved. As an example, carrier sleeves comprising a window can be built in, so that a visual observation or a turbidity measurement can be performed.

11 Claims, 3 Drawing Sheets

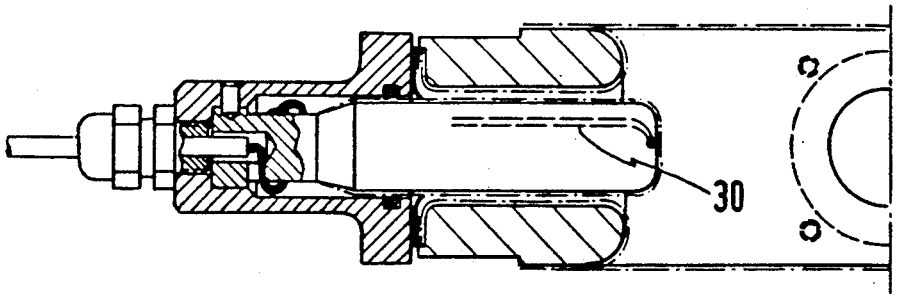
FIG. 7a
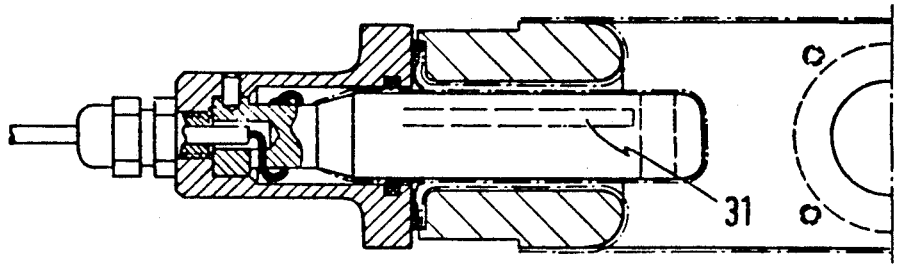
FIG. 7b
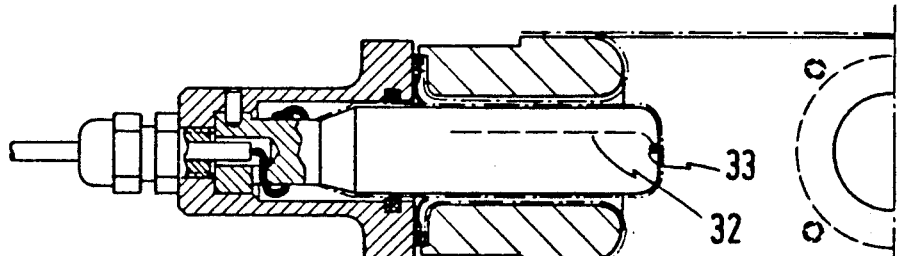
FIG. 7c
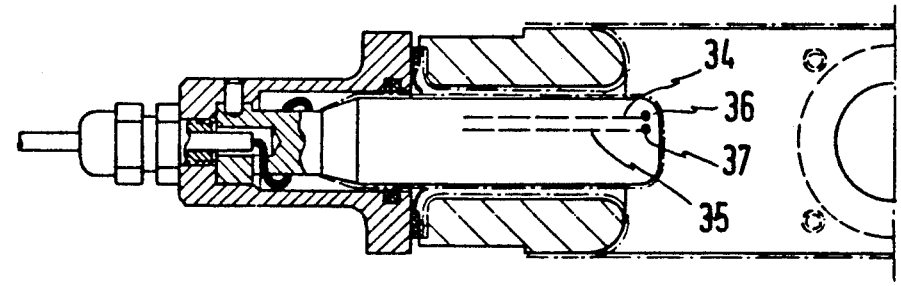
FIG. 7d
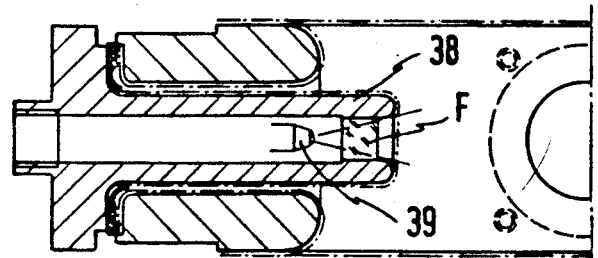
FIG. 7e
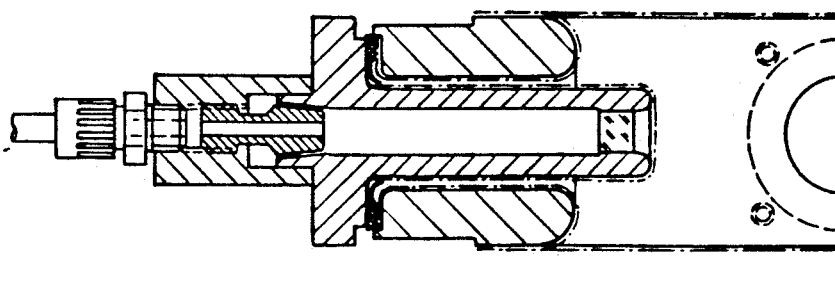
FIG. f

ARRANGEMENT OF PROBES

The invention is related to an arrangement of probes for a measuring device, with which especially a continuous supervision of properties of a medium is possible flowing through a pipe line.

Such supervisions are often necessary out of reasons related to environment protection, since it is only permitted to discharge sewage water if certain limit values with respect to pH-value, turbidity, temperature etc. are observed. Numerous measuring devices having different designs are known, which can be used for such purposes. As an example, for a turbidity measurement in a pipe line two windows can be provided on diametrically opposite sides of a tubular element, so that on the one side a light source and on the other side a receiving optics may be arranged. If such a measuring device shall be provided on an enamelled pipe line, a rather high expenditure with respect to the design is needed, in order that it is possible to provide opposite windows on a tubular element. Even more difficulties result, if for the respective supervision several measuring devices are needed.

It is therefore object of the invention to provide an arrangement of probes, which allows with a rather small expenditure with respect to design and work, to provide in a pipe line to be supervised a relatively large number of different measuring probes in connection with measuring devices, which can be connected therewith.

This problem is solved by an arrangement of probes in accordance with the subject of the present invention. Advantageous embodiments of the invention are subject of the various aspects of the present invention.

Therefore, such an arrangement of probes comprises a carrier formed as an intermediate flange, which carrier can be also mounted in a pipe line after the pipe line has been installed. The intermediate flange, which can have an axial length of less than 100 mm, can be arranged without difficulties between the flange surfaces of two adjacent tubes, and can be fixed sealingly with a usual loose flange connection. At such a carrier with an inner diameter of about 150 mm it is possible to provide e.g. eight radially extending mounting openings, so that a number of probes corresponding to given requests can be mounted. Since the measuring probes can be arranged exchangeably, combinations of probes can be provided corresponding to practically any number of requests For measuring probes and other units of measuring devices not needed mounting openings can be closed with a dummy plug. The shown embodiment is having a design of the carrier which can be enamelled, so that the inner surfaces of the carrier including the mounting openings, which surfaces can be contacted by the product medium, can be provided with a corrosion resistant enamel. In order to achieve an increased mechanical rigidity in comparison to mechanically delicate measuring probes, preferably enamelled measuring probes consisting out of steel are used. The fundamental design of enamelled measuring probes is known per se (e.g. German Patents 21 33 419 and 27 21 939). For the present purpose of use a further development of such probes has been made, in order that such probes have a sufficiently small diameter and fastening means adapted for mounting.

Because of the use of an electrically insulating corrosion resistant layer it is possible with rather simple means to separate the individual measuring devices electrically from each other The connecting leads of the individual measuring probes can be connected by plug connections with a connection box having terminals to be connected with known measuring transducers, to which display-, recording-, and alarm-devices etc. of interest can be connected The measuring values of the individual measuring probes serving as transmitter can be interconnected with each other over a micro processor.

The arrangement of probes can be used besides for a control in pipe lines for sewage water also for other purposes of use, e.g. in other pipe lines in the chemical industry, in tube- or loop-reactors for supervising and controlling the operating sequence of processes, or in flue gas sulfur removal installations for controlling the amount of contained solids, of the pH-value etc. of the washing liquid in the circulation-conduits.

The present invention comprises apparatus for holding a plurality of measuring probes, comprising a housing of generally polygonal shape having a plurality of radially extending mounting openings with planar mounting surfaces surrounding each opening adapted for exchangeably and sealingly mounting such probes, the housing having an inner surface of electrically insulating corrosion resistant material. Another aspect of the present invention comprises such apparatus wherein the housing has at least two diametrically opposed mounting openings in each of which a carrier sleeve provided with a window is arranged. Alternatively, an additional carrier sleeve may be provided with a window and may be arranged in a mounting opening which is spatially displaced 45° with respect to one of the two diametrically opposed mounting openings. In regard to the carrier sleeves, above, a light source may be arranged in one of them and a light receiver may be arranged in another for the purpose of measuring turbidity. In regard to the mounting openings described above, they may be adapted to exchangeably and sealingly mount a dummy plug or a measuring probe. The housing described above may have eight mounting openings arranged octogonally and that housing may have a circular inner shape having a diameter of approximately 150 millimeters. The electrically insulating corrosion resistant material may be enamel-coated steel. The present invention may include measuring probes in combination with the housing wherein each measuring probe has a body which is coated with enamel to insulate that probe from the housing. The dummy plug, likewise, may be coated with enamel to insulate it from the housing. One or more of the carrier sleeves may be provided with a fiber optic endoscope.

Figure 2:
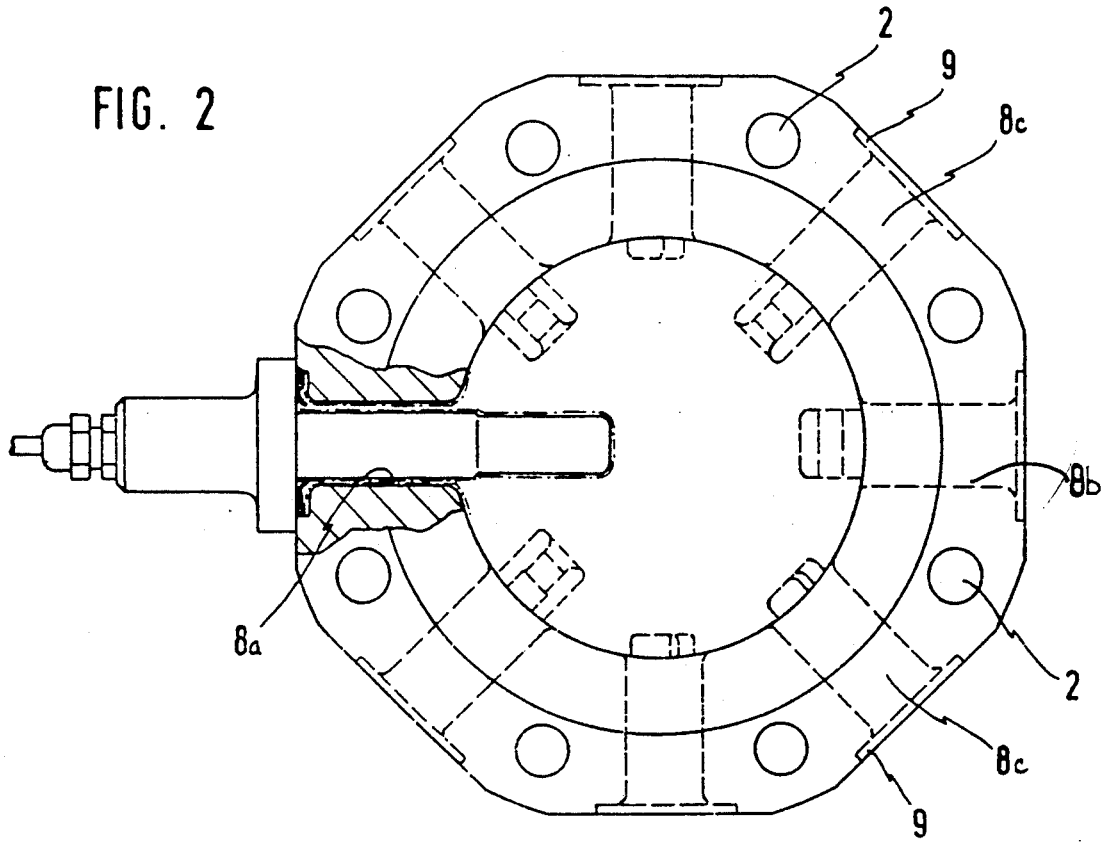
Figure 3:
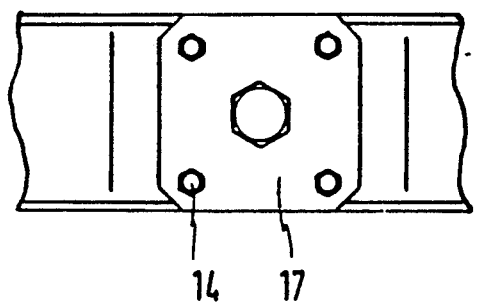
Figure 4:
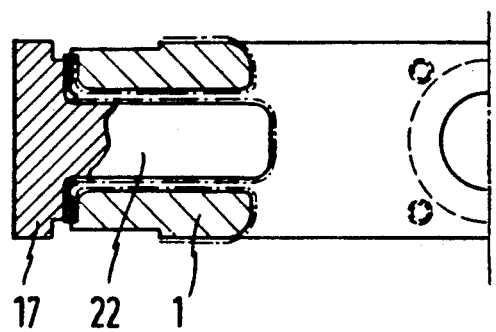
Figure 5:
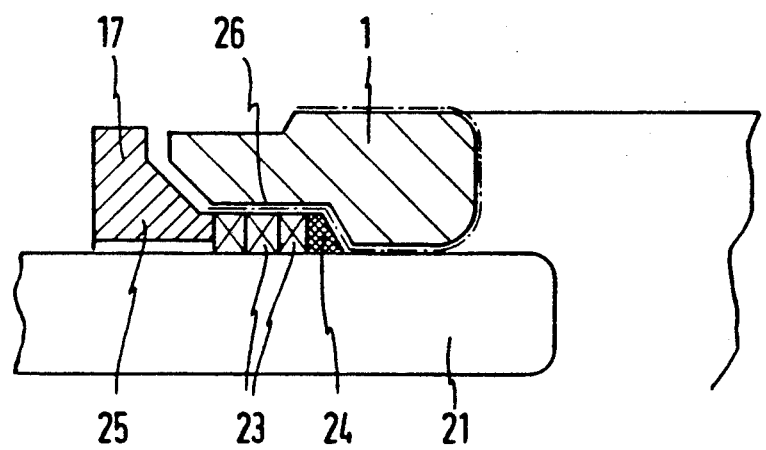
Figure 6:
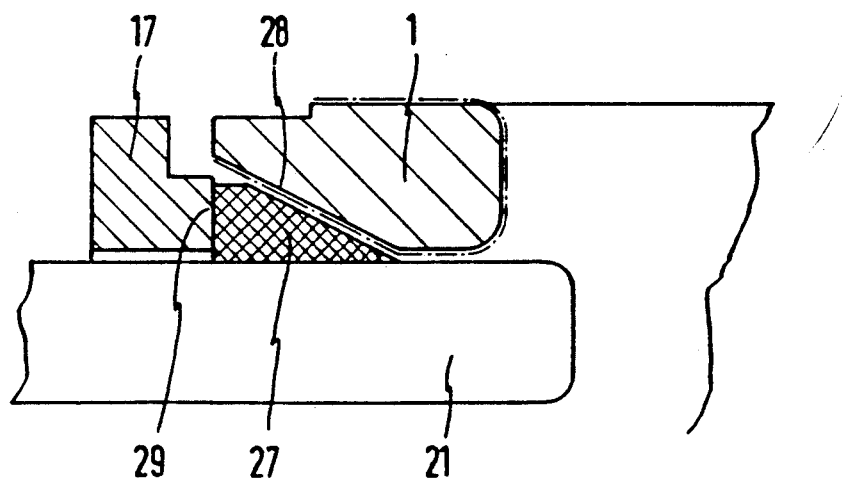

On the basis of the drawings a specific embodiment of the invention shall be described. In the drawings:

FIG. 1 and 2 show a sectional view and a plan view,- resp., of a carrier in accordance with the invention, FIG. 3 shows a view of a mounted measuring probe from the left side in FIG. 2, FIG. 4 shows a sectional view through a dummy plug mounted in a mounting opening in FIG. 1 and 2, FIG. 5 shows a sectional view of a modified embodiment of the sealing means in FIG. 1 and FIG. 2, FIG. 6 shows a sectional view corresponding to FIG. 5 of a further modified embodiment of the sealing means, and FIG. 7a–7f show embodiments of different enamelled measuring probes, which are inserted into a mounting opening.

In the embodiment as shown in FIG. 1 a carrier 1 is provided, which is formed as an intermediate flange having eight bores 2, so that the carrier 1 can be mounted by means of a loose flange connection 4 and 5 between flanges 6 and 7 of adjacent tube elements of a pipe line. Between all of the adjacent flange surfaces in each case a gasket is inserted. The inside of the pipe line appearing in outlines is enamelled.

The shown carrier 1 may have e.g. an inner diameter of 150 mm and a thickness of 65 mm. Eight mounting openings 8 are provided, each having a plane mounting surface 9 surrounding its outer end. The measuring probe 21 shown in FIG. 1 is a pH-probe having an enamelled body 20. The outer end of the body 20 is surrounded by a carrier sleeve 12, through which a securing pin 13 protrudes into the body of the probe. The connection lead of the probe is fixed to the carrier sleeve by means of a retaining nut 15. The carrier sleeve 12 is having a mounting flange 17, at which a surface is formed fitting against the mounting surface 9. As may be seen from FIG. 3, the mounting flange 17 can be detachably connected with the mounting surface 9 of the carrier by means of four screws 14. For sealing purposes an O-ring 10 and a lip sealing 11 are provided.

The carrier 1 serving as intermediate flange is having an outline corresponding to a polygon with eight sides and is having a design which can be enamelled, so that as an electrically insulating corrosion resistant layer an enamel layer 16 can be provided, protecting the surfaces of the carrier which can come into contact with the product medium. At the outer ends of the mounting openings 8 the enamelling extends to the mounting surface 9, so that the surface region extending to the contact region of the lip sealing 11 is protected against corrosion.

FIG. 5 shows an embodiment modified in comparison to the embodiment of the sealing means shown in FIGS. 1 and 2. Instead of the O-ring 10 and the lip sealing 11 in FIG. 1 a stuffing box is provided for the embodiment in FIG. 5, which is preferably in the case of high-duty chemical conditions. The stuffing box comprises packing rings 23 and a base ring 24 out of PTFE or the like material providing protection against corrosive media flowing through the pipe line. In this embodiment the mounting flange 17 is formed in such a manner, that it provides for the function of the gland of the stuffing box. Therefore, the mounting flange is having an annular projection 25 adjacent to the outer end of the packing rings 23, so that the packings rings and the base ring 24, which are arranged in an annular notch 26, are in sealing contact with the adjacent enamel surface on the carrier 1 formed as an intermediate flange.

FIG. 6 shows another embodiment of the sealing means which can be used in the case of higher chemical loads. In this embodiment a wedge ring 27 out of PTFE or the like corrosion resistant material is provided. The outer end of the respective mounting opening in the carrier 1 is having a conical enlargement 28, so that by means of an annular projection 29 at the mounting flange 17 the wedge ring 27 can be pressed sealingly against the enamelled surface in the region of the conical enlargement 28 and against the adjacent enamel surface of the probe 21. Preferably the outer end of the respective mounting openings in the embodiments in FIGS. 5 and 6 are formed in such a manner, that also the dummy plug 22 shown in FIG. 4 can be mounted in a well sealing manner.

For the sealings in FIGS. 5 and 6 preferably helical springs are provided under the heads of the screws 14 in FIG. 3.

In FIGS. 7a to d and 7f different enamelled measuring probes are shown, which can be inserted into the mounting openings. FIG. 7e shows a mounted carrier sleeve for a glass window.

The enamelled measuring probe shown in FIG. 7a serves for a temperature measurement and comprises for this purpose a thermoelement 30, which is embedded into the enamel layer and shown in dashed lines.

FIG. 7b shows an enamelled measuring probe for performing a capacity-measurement on the basis of the capacitor-principle. Into the enamel layer of the measuring probe an electrically conducting layer 31 is embedded, which serves together with the metallic body of the measuring probe as capacitor. With such a measuring probe the dielectric constant of the medium flowing through the pipe line can be determined or it can be detected, if the pipe line is empty.

FIG. 7c shows a rH-measuring probe with an electrode 32 embedded into the enamel layer, the end 33 of which electrode is in electrically conducting connection with the medium in the pipe line.

FIG. 7d shows a measuring probe having one or two electrodes 34,35 embedded into the enamel layer, the end surfaces 36,37 of which electrodes are in an electrically conducting connection with the medium in the pipe line. By means of an associated measuring device a continuous supervision can be performed, if pores or other damages of the enamel layer of an enamelled pipe line exist. For a supervision of enamelled pipe lines having a length of 100 m or more, preferably the second electrode is arranged at the end of a supervision region along the length of the pipe line, so that e.g. in the case of the use of a constant current source, the positive pole of which is connected with the carrier material of the pipe line and the negative pole of which is connected with the two electrodes, a localization of the enamel damage can be performed by means of a measurement of a potential difference. Such a supervision is especially then of interest, if the electrically conducting medium is highly corrosive, so that in the case of enamel damages the medium would leak out of the pipe line in the region of the damage after a rather short time. Since it is possible to localize an enamel damage with such a measuring device, it can be determined by means of the measuring device, which of the tube elements of the pipe line consisting of several tube elements has to be exchanged.

FIG. 7e shows a mounted carrier sleeve 38 for a glass window F. The outer surface of the carrier sleeve 38 and also the forward end region of the carrier sleeve may be enamelled, and the outer surface of the cylindrical glass body forming the window F can be fused with the enamel layer. If in two diametrically opposite mounting openings 8 in FIG. 2 two carrier sleeves with a window F are mounted, a sight glass arrangement is provided allowing a visual observation. Such diametrically opposed carrier sleeves 38 with a window F allow in an advantageous manner to perform a turbidity measurement, For performing a method with transmitted light, two diametrically opposite carrier sleeves 38 with a window F are provided, whereby in one of the carrier sleeves a light source 39 and in the diametrically opposite carrier sleeve a not shown light receiver can be arranged. Furthermore a turbidity measurement with a method using stray light is possible, if a third carrier sleeve 38 is inserted into the mounting opening 8c in FIG. 2, which opening is offset for 45° to the mounting opening 8b of the two diametrically opposite mounting openings 8a, 8b. In this third carrier sleeve a not shown receiver for stray light can be arranged. A specific advantage of the invention is therefore also to be seen in the fact, that methods with transmitted light or stray light can be performed by means of a single carrier 1 if desired, which can be manufactured in a rather simple manner with a design allowing enamelling.

In order to achieve a reliable sealing of the window, it is also possible to shrink a glass disk into the carrier sleeve 38 having an enamelled inner surface, by providing auxiliary means for sealing. Since such a window may have a rather small diameter of about 8 mm, a visual observation of the turbidity etc. of the flowing medium is not easily possible with sufficient distinctiveness. Therefore it is advantageous to insert a fiber optics in the form of an endoscope. Therewith a very good observation of the flowing medium is possible.

In the case of higher temperatures it is furthermore advantageous not to arrange the light receiver and the light source in the carrier sleeve for performing the turbudity measurement. Therefore it is also advantageous in this case to use a fiber optics, so that the light source and the light receiver can be arranged in a distance from the probe.

FIG. 7f shows a probe serving a reference system, which is e.g. necessary for performing measurements of the pH-value. Thereby the glass body is shrunk into the carrier sleeve enamelled along its inner surface, whereby the shrinking surface is serving as diaphragm. A pH-measurement is performed by means of the probe 21 in FIG. 1, at which probe a forward circumferential region is provided with an ion-sensitive enamel layer.

What is claimed is:

1. Apparatus for holding a plurality of measuring probes, comprising a housing of generally polygonal shape having a plurality of radially extending mounting openings with planar mounting surfaces surrounding each opening adapted for exchangeably and sealingly mounting said probes, said housing having an inner surface of electrically insulating corrosion resistant material, wherein said housing has eight mounting openings arranged octagonally and wherein said housing has a circular inner shape having a diameter of about 150 millimeters.

2. Apparatus as recited in claim 1 wherein said housing has at least two diametrically opposed mounting openings in each of which a carrier sleeve provided with a window is arranged.

3. Apparatus as recited in claim 2 wherein an additional carrier sleeve provided with a window is arranged in a mounting opening which is spatially displaced 45° with respect to one of said two diametrically opposed mounting openings.

4. Apparatus as recited in claim 3 wherein a light source is arranged in one of said carrier sleeves and a light receiver is arranged in another said carrier sleeve for the purpose of measuring turbidity.

5. Apparatus as recited in claim 3 wherein said carrier sleeve is provided with a fiber optic endoscope.

6. Apparatus as recited in claim 2 wherein a light source means is arranged, in one of said carrier sleeves, and a light receiver means is arranged in another said carrier sleeve for the purpose of measuring turbidity.

7. Apparatus as recited in claim 2 wherein said carrier sleeve is provided with a fiber optic endoscope.

8. Apparatus as recited in claim 1 wherein said mounting openings are adapted to exchangeably and sealingly mount a dummy plug or a measuring probe.

9. Apparatus as recited in claim 8 wherein said dummy plug is coated with enamel to insulate said plug from said housing.

10. Apparatus as recited in claim 1 wherein said electrically insulating corrosion resistant material is enamel-coated steel.

11. Apparatus as recited in claim 1 and including at least one measuring probe in combination with said housing wherein each said measuring probe has a body which is coated with enamel to insulate said probe from said housing.

* * * * *